(12) United States Patent
Iwashita et al.

(10) Patent No.: US 8,388,761 B2
(45) Date of Patent: Mar. 5, 2013

(54) METHOD FOR CONTAINER STERILIZING AND WASHING AND APPARATUS THEREFOR

(75) Inventors: Takeshi Iwashita, Yokohama (JP); Nobuaki Nagatani, Yokohama (JP); Kenichi Kominami, Yokohama (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 546 days.

(21) Appl. No.: 12/304,095

(22) PCT Filed: Jun. 9, 2006

(86) PCT No.: PCT/JP2006/311655
§ 371 (c)(1),
(2), (4) Date: Dec. 9, 2008

(87) PCT Pub. No.: WO2007/141881
PCT Pub. Date: Dec. 13, 2007

(65) Prior Publication Data
US 2010/0229895 A1    Sep. 16, 2010

(51) Int. Cl.
*B08B 9/32* (2006.01)
(52) U.S. Cl. ........... 134/22.18; 134/23; 134/26; 134/28; 134/30; 134/166 R; 422/28; 422/303
(58) Field of Classification Search ........................ None
See application file for complete search history.

(56) References Cited

U.S. PATENT DOCUMENTS

2002/0085971 A1* 7/2002 Raniwala ....................... 422/303
2003/0165400 A1* 9/2003 Hayakawa et al. ............ 422/28

FOREIGN PATENT DOCUMENTS

| JP | 59150797 U    | 10/1984 |
|----|---------------|---------|
| JP | 8-323312 A    | 12/1996 |
| JP | 2000-147732 A | 5/2000  |
| JP | 2001-39414 A  | 2/2001  |
| JP | 2005-170393 A | 6/2005  |
| JP | 2005-211779 A | 8/2005  |
| JP | 2006-89146 A  | 4/2006  |

OTHER PUBLICATIONS

Notification of Transmittal of Translation of the International Preliminary Report on Patentability (Form PCT/IB/338) of International Application No. PCT/JP2006/311655 mailed Jan. 22, 2009 with Forms PCT/IB/373 and PCT/ISA/237.
International Search Report of PCT/JP2006/311655, Mailing Date of Jul. 18, 2006.

* cited by examiner

*Primary Examiner* — Michael Barr
*Assistant Examiner* — Caitlin N Dunlap
(74) *Attorney, Agent, or Firm* — Westerman, Hattori, Daniels & Adrian, LLP

(57) ABSTRACT

When the inner surface of containers conveyed in an inverted posture is sterilized, the sterilization efficiency can be increased, the amount of sterilizing fluid used can be reduced, the sterilization time and washing time can be shortened, the number of drive components of the apparatus can be reduced and the apparatus can be simplified and reduced in cost. A non-inserted nozzle 20 is disposed at a distance of 1-50 mm below the lower end surface 52 of a mouth of a container conveyed in an inverted posture, the sterilizing fluid is mixed with air and the sterilizing fluid is atomized and sprayed intermittently from the non-inserted nozzle toward the inside of the container.

9 Claims, 5 Drawing Sheets

Fig. 3-A
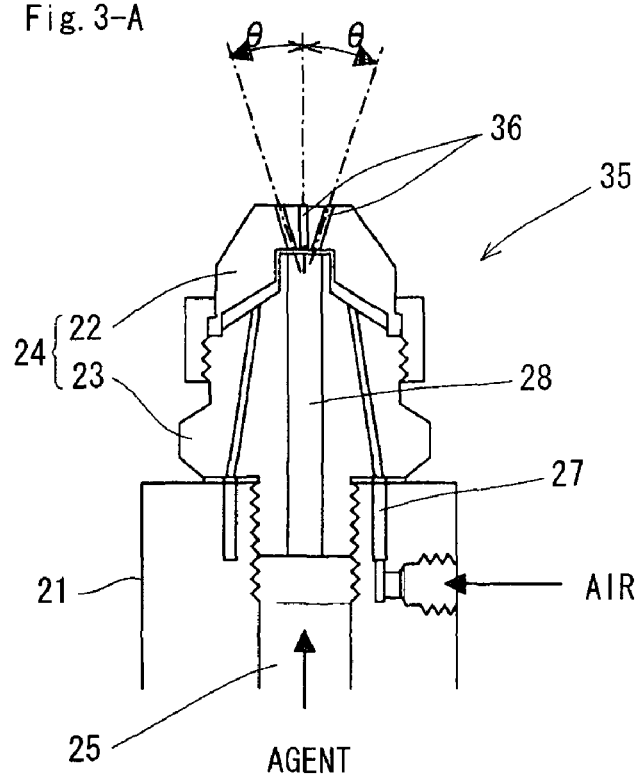
Fig. 3-B
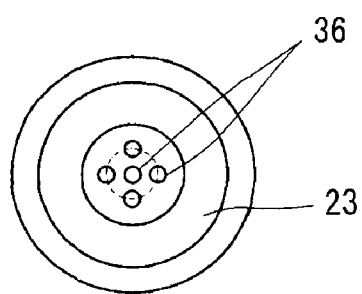
Fig. 4-A
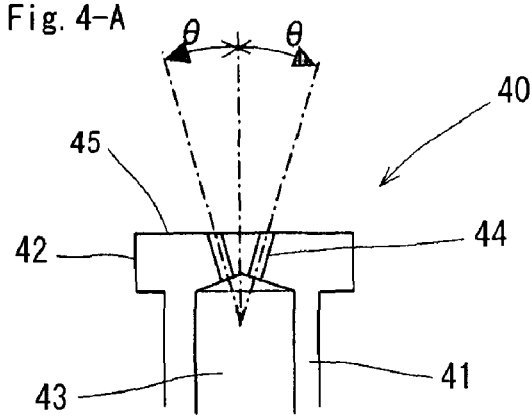
Fig. 4-B
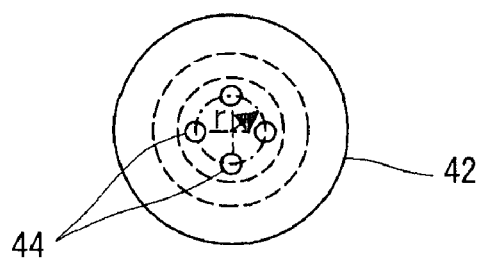

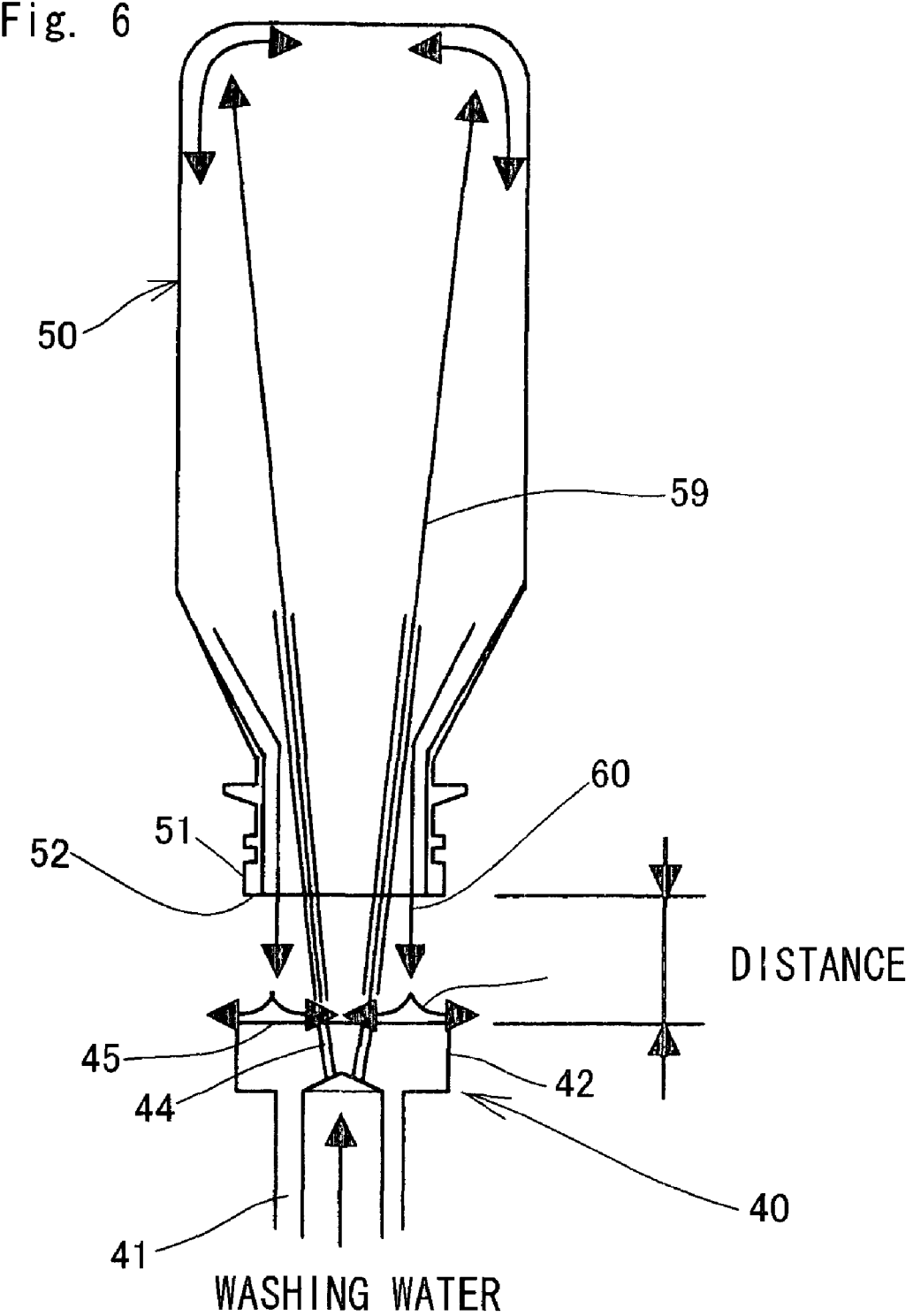

METHOD FOR CONTAINER STERILIZING AND WASHING AND APPARATUS THEREFOR

FIELD OF THE INVENTION

The present invention relates to a method for sterilizing and washing containers in a filling and sealing process in which contents liquid is filled and sealed into the containers and to an apparatus therefor, and more particularly to a method for sterilizing and washing containers that is suitable for an aseptic filling system and to an apparatus therefor.

BACKGROUND ART

A method in which containers are sterilized in an inverted posture by using an aqueous solution of peracetic acid has been widely used for sterilizing bottles in an aseptic filling system. This sterilization method generally employs a procedure in which a bottle is held in an inverted posture, a spraying nozzle is inserted into the bottle mouth, and a sterilizing fluid is sprayed at least as a straight stick-like flow on the inner surface of the bottle, but the sterilization effect of the inside of the container in this method depends on whether the sprayed sterilizing agent or washing water directly collides with the inner surface of the container or the inner surface of the container is wetted when the liquid flows down along the inner surface of the container after the collision with the surface. The resultant problem is that if the flow rate is decreased, then uniform wetting characteristic of the inner surface of the bottle is deteriorated and sterilization is incomplete. For this reason, a large quantity of sterilizing fluid has to be sprayed inside the container within the predetermined time. Furthermore, in the case of synthetic resin containers such as PET bottles, complex concave-convex shape, such as reinforcing ribs, are present on the bottom and body section to increase the rigidity of container. Therefore, a large quantity of sterilizing fluid has to be sprayed over a long period in order to wet uniformly the entire inner surface of the container, thereby hindering the transition to speedup of lines that has been urgently required in recent years. Furthermore, that a large quantity of sterilizing fluid is required causes waste of the sterilizing fluid and high cost. Moreover, in the washing process, the sterilizing fluid (sterilizing liquid) that has adhered to the inner surface of the container in the sterilization process has to be completely washed off. Accordingly, the washing water has to come into contact with the entire inner surface of the container, in the same manner as in the sterilizing process in order to wash off the sterilizing liquid, and there are the problems that are similar to that in the sterilizing process.

In order to solve the above-described problems, the inventors have suggested a method by which the contact ratio of a sterilizing fluid with the inner surface of a bottle is increased and sterilization is conducted with high efficiency in which a first spraying hole is formed in the center of a distal end section of a spraying nozzle that is to be inserted into the mouth of the inverted bottle and a second spraying hole is formed to be circumferentially opened below the first spraying hole, the liquid sprayed from the two spraying holes toward the bottom section of the container flows down, and part of the liquid is stirred and pushed up by the sterilizing fluid sprayed from the second spraying hole and scattered over the inner surface of the bottle (ref. Patent Document 1).

A method for washing and sterilizing containers according to which a nozzle having a section to collect liquid is disposed below a container mouth, a mist or liquid flow supplied from a spraying hole of the nozzle is brought into contact with a reflux flow, and the distal end of the mist or liquid flow that collides with the inner surface of the container is constantly oscillated over the inner surface of the bottom section of the container has also been suggested as a method for sterilizing or washing a container in which the container is held in an inverted posture and a nozzle is not inserted into the container (ref. Patent Document 2).

Patent Document 1:
  Japanese Patent Application Laid-open No. 2003-181404
Patent Document 2:
  Japanese Patent Application Laid-open No. 6-121974

DISCLOSURE OF THE INVENTION

Problem to be Solved by the Invention

The above-described former sterilizing method and apparatus had a higher sterilization efficiency than a method in which the inner surface of a container was sterilized by simply spraying a stick-like flow of a sterilizing fluid inside the container and made contribution to saving the sterilizing fluid, but as the spraying nozzle was inserted into the container mouth to spray the sterilizing fluid, a lifting device for inserting a spraying nozzle into the mouth of the container was required, and the mechanism of the apparatus was complicated and the cost was increased, and the time had to be ensured for inserting the spraying nozzle into the container mouth and removing the nozzle therefrom, thereby hindering the speedup of lines, and as the spraying nozzle was frequently raised and lowered, the problems to be solved lie in endurance, maintenance, and inspection of the apparatus. Furthermore, with simple spraying of the sterilizing fluid, the ratio of the sterilizing fluid that contributes to wetting the inner surface of the container is small by comparison with a large amount of sterilizing fluid required and a problem requiring resolution is also associated with a large waste of the sterilizing fluid. There are also same problems in the washing method and apparatus in which a spraying nozzle is inserted into the mouth of the container, washing water is sprayed by the spraying nozzle, and the inside of the container is washed. On the other hand, with the latter method the nozzle is not inserted into the container, the mechanism is simple and the line speed is increased. However, because the irregular oscillations of the atomized liquid flow are used so as to carry out uniform contact of the sterilizing fluid with the inner surface of the container, there are two periods in which the liquid falls and the liquid does not fall on the bottom section of the container and the process lacks certainty effect.

Accordingly, an object of the present invention is to provide a method and an apparatus for sterilizing and washing the inner surface of a container conveyed in an inverted posture, wherein the sterilizing fluid can be uniformly and surely brought into contact with the inner surface of the container, and the sterilizing efficiency can be increased, and the amount of sterilizing fluid can be reduced, and the sterilization process time can be shortened, and the number of drive units of the apparatus can be decreased, and the apparatus can be simplified and reduced in cost.

Means for Solving Problem

The method for sterilizing and washing a container in accordance with the present invention that resolves the above-described problems comprises a step of sterilizing and a step of washing the inner surface of a container that is conveyed in an inverted posture, wherein in the sterilizing step a non-inserted nozzle is disposed below a mouth of the container conveyed in an inverted posture at a distance of 1 to 50 mm therefrom, and a sterilizing fluid and air are mixed and sprayed from the non-inserted nozzle into the inner surface of the container, and sterilizing fluid is atomized to wet the inner surface of the container to be sterilized.

The amount of the sterilizing fluid used can be further cut down without ruining the sterilizing effect by alternately spraying the sterilizing fluid and halting the spraying and such procedure is preferred. The sterilizing fluid may be any one from warm water, an aqueous solution of peracetic acid, an aqueous solution of hydrogen peroxide, and an aqueous solution containing hypochlorous acid, and the optimum sterilizing fluid may be selected according to the type and shape of the container and the type of the contents liquid. Providing a container preheating step of preheating the container prior to the sterilization step makes it possible to prevent the drop in temperature of the sterilizing fluid when it comes into contact with the inner surface of the container and increase the sterilization efficiency. Furthermore, during sterilization processing of the inner surface of the container, a heated sterilizing fluid may be sprayed from one or a plurality of sterilizing nozzles toward the outer surface of the container, and the outer surface of the container may be sterilized by wetting the outer surface of the container with the atomized sterilizing fluid, whereby the inner and outer surfaces of the container can be sterilized more efficiently. In order to increase further the sterilization efficiency, it is preferred that the container surface temperature in the sterilization step be adjusted to 45 to 90° C. The temperature adjustment method involves, for example, covering the path through which the container passes during the sterilization processing with a tunnel-like shielding material, heating the inside of the tunnel-like shielding material, and spraying the sterilizing fluid while maintaining the heated atmosphere. Furthermore, it is also preferred that in the washing step, a non-inserted nozzle be disposed below a mouth of the container conveyed in an inverted posture at a distance of 5 to 50 mm therefrom, washing water is sprayed from the non-inserted nozzle into the container, and the inner surface of the container is washed.

The container sterilizing and washing apparatus in accordance with the present invention that is designed for implementing the above-described method comprises sterilizing means for sterilizing with a sterilizing fluid the inner surface of a container conveyed in an inverted posture and washing means with using washing water, wherein the sterilizing means has container transfer means comprising a plurality of turrets for transferring the container in an inverted posture and sterilizing fluid spraying means for spraying a sterilizing fluid on the inner surface of the inverted container transferred by the transfer means, and the sterilizing fluid spraying means is a non-inserted nozzle disposed at a distance of 1 to 50 mm below an open mouth of the container conveyed by the container transfer means. The washing means has container transfer means comprising a plurality of turrets for transferring the container in an inverted posture and washing water spraying means for spraying washing water on the inner surface of the inverted container transferred by the transfer means, and the washing water spraying means is a non-inserted nozzle disposed at a distance of 5 to 50 mm below an open mouth of the container conveyed by the container transfer means.

The non-inserted nozzle is preferably a spraying nozzle having an inner mixing chamber for mixing a sterilizing fluid or washing fluid and air inside the nozzle and atomizing and spraying the sterilizing fluid or washing fluid. In another embodiment, the non-inserted nozzle is preferably a spraying nozzle having an inner mixing chamber for mixing a sterilizing fluid or washing fluid and air inside the nozzle and atomizing and spraying the sterilizing fluid or washing fluid, this nozzle having a plurality of nozzle holes, and the nozzle holes being disposed on a circle so as to be inclined outwardly in a direction upward or downward.

EFFECT OF THE INVENTION

In accordance with the present invention, a non-inserted nozzle is disposed so as to be at a distance of 1 to 50 mm below the mouth of a container conveyed in an inverted posture and the sterilizing fluid and air are mixed and the sterilizing fluid is atomized and sprayed toward the inner surface of the container. Therefore, even in a container with concave-convex shape on the inner wall surface, the inner surface of the container can be almost uniformly wetted with the sterilizing fluid with good stability during spraying, and the sterilization efficiency is high and the amount of the sterilizing fluid used can be reduced. Furthermore, as the sterilizing fluid can be sprayed inside the container without inserting the nozzle into the mouth of the container, it is not necessary to use a lifting mechanism for lifting and lowering the non-inserted nozzle, and the sterilization time can be shortened, and the number of drive parts of the apparatus can be reduced, and the apparatus can be simplified and reduced in cost. Moreover, by spraying the sterilizing fluid intermittently, the sprayed amount of the sterilizing fluid can be reduced without deteriorating the sterilization effect that is obtained in the case of continuous spraying.

BRIEF DESCRIPTION OF THE DRAWINGS

FIG. 3 is a main cross-sectional view of a non-inserted nozzle for sterilization of another embodiment of the present invention;

FIG. 4-A is a front sectional view of a non-inserted nozzle for washing of an embodiment of the present invention; FIG. 4-B is a plan view thereof;

FIG. 6 is a schematic drawing illustrating a container washing method using the non-inserted nozzle for washing shown in FIG. 4.

Figure 1:
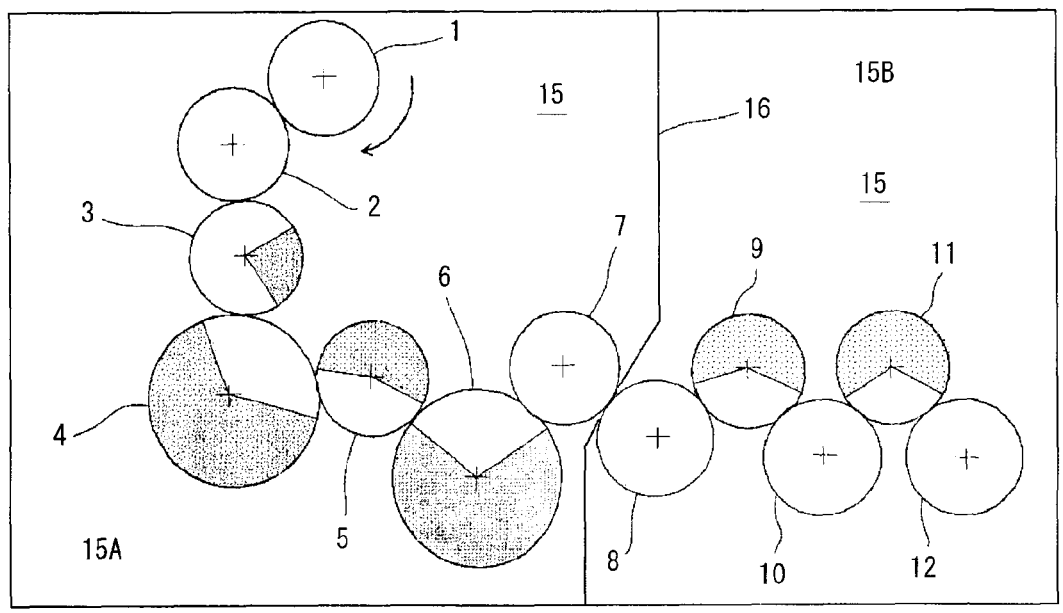
FIG. 1 is a simplified drawing illustrating the arrangement of the container sterilizing and washing apparatus of an embodiment of the present invention.

EXPLANATIONS OF LETTERS OR NUMERALS 1. supply turret
2. bottle reversion turret
3. preheating turret
4. 5. 6. sterilizing turret
7. discharge turret
8. transfer turret
9. 11. washing turret
10. drain turret
12. drain and transfer turret
20. 35. non-inserted nozzle in the sterilizing process
40. 46. non-inserted nozzle in the washing process
21. 41. nozzle stem
22. nozzle sleeve
23. cap
24. 42. nozzle mouth
25. 43. sterilizing fluid channel -continued

| EXPLANATIONS OF LETTERS OR NUMERALS | |
|---|---|
| 31. mixing chamber | 32. 36. orifice |
| 44. nozzle hole | 45. 47. liquid-receiving surface |
| 50. bottle | 59. sprayed liquid |
| 60. reflux liquid flow | |

DESCRIPTION OF THE PREFERRED EMBODIMENT

FIG. 1 is a schematic drawing illustrating the arrangement of turrets of a container sterilizing and washing apparatus in an aseptic filling process of the present embodiment. In the case of a container sterilizing apparatus of the conventional turret system, the turret diameter has to be increased in order to arrange an inversion zone for reversing a container into an inverted posture, a container sterilizing zone, a drain zone for draining a sterilizing fluid, a reversion zone for turning the container from the inverted posture into an upright state, or a container discharge zone around one large-diameter turret. In particular, because the recently developed high-speed filling lines have a large number of heads, and large turrets with a diameter above 3 m are necessary, and large space is required, and the cost of energy required to drive the turret is increased. In the present embodiment, in order to save space, the turret is divided into a plurality of small-diameter turrets for each respective function, and the combination of such turrets makes it possible to reduce size, and decrease occupied space, and reduce energy consumption of the entire apparatus, and increase the sterilization efficiency and washing efficiency, and reduce the amount of sterilizing fluid and washing water used in the process. Furthermore, by unitizing the combination of comparatively small turrets of different diameter, mold replacement is facilitated when the molds have to be replaced according to the type of container to be sterilized and the system flexibility is improved. Furthermore, by combining a large number of turrets, the sterilization process is divided into steps and the sterilizing nozzle shape or spraying conditions of each step can be changed, whereby the sterilization can be conducted more efficiency and the consumption of the sterilizing agent can be reduced.

The embodiment shown in FIG. 1 illustrates a container sterilizing and washing apparatus in an aseptic filling system. The apparatus comprises a combination of a large number of small turrets and the entire system is accommodated inside an aseptic chamber 15. The aseptic chamber 15 is further divided into a sterilization chamber 15A and a washing chamber 15B and partitioned by a partition wall 16, except a transfer zone of the below-described turret 7 and turret 8. The air in the sterilization chamber 15A does not flow into the washing chamber 15B.

In the figure, the reference numerals 1 and 2 stand for a bottle supply turret and a bottle reversion turret, respectively. A bottle supplied in an upright state to the bottle supply turret 1 is reversed by a well-known reversion mechanism when the bottle is transferred to the bottle reversion turret 2. The reference numeral 3 stands for a preheating turret. This turret serves to preheat the container prior to a sterilization process to spray a sterilizing fluid so as to prevent the sterilizing fluid from being cooled rapidly on contact with the container during sterilization. In the turret, nozzles for spraying the heated sterilizing fluid are arranged along a bottle conveying line and the heated sterilizing fluid is sprayed on the outer surface of the container to preheat the container and sterilize the outer surface of the container. Alternatively, a heating means such as a hot air blower or heater may be appropriately arranged as another preheating means.

The reference numerals 4 to 6 stand for sterilization turrets. In the present embodiment as described hereinbelow, the below-described non-inserted nozzles are arranged below the pockets of turrets so that the sterilizing fluid (sterilizing liquid) can be sprayed from below and outside of the bottle mouth on the inner surface of the bottle. In the apparatus of the present embodiment, the non-inserted nozzles are configured as spraying nozzles for mixing and spraying the sterilizing agent and air. Furthermore, in the present embodiment, the sterilization process is divided between three turrets with mutually different diameters, each sterilization turret having different sterilization time. For example, Provided that the sterilization time of the container in the sterilization turret 4 is 3 sec, the sterilization time in the sterilization turret 5 is 2 sec, the sterilization time in the sterilization turret 6 is 3 sec, if the time of transfer between the turrets is 1 sec, then spraying of the sterilizing fluid onto the container is performed intermittently to sterilize the inner surface of the container in the manner as follows: performed for 3 sec, stopped for 1 sec, performed for 2 sec, stopped for 1 sec, and performed for 3 sec if the sterilization time of the container in the sterilization turret 4 is 3 sec, the sterilization time in the sterilization turret 5 is 2 sec, the sterilization time in the sterilization turret 6 is 3 sec. Furthermore, nozzles for outer surface sterilization that spray the sterilizing fluid on the outer surface of the container are arranged along the container conveying line of those sterilization turrets.

The reference numeral 7 stands for a sterilizing fluid discharge turret, 8 stands for a transfer turret for transferring the sterilized bottle to a washing turret, and the reference numeral 9, 11 stand for washing turrets. Non-inserted nozzles for spraying aseptic water into the bottles are disposed below the pockets of the washing turrets so as to spray the water on the inner surface of the bottles from below and outside the bottles, in the same manner as the non-inserted nozzles in the sterilizing process. The reference numeral 10 stands for a drain turret. The reference numeral 12 stands for a transfer turret also serving as a drain turret; this turret reverses the washed bottles from the inverted posture into the upright state and supplies them into the next filling apparatus. In the bottle sterilizing and washing apparatus of the present embodiment, using a large number of small-diameter turrets in the above-described manner makes it possible to reduce the installation area by comparison with the arrangement of conventional large-diameter turrets, to modularize the turrets, and to change easily the combination of sterilizing time and washing time according to the type of the container.

The blackened segments in the turrets of the sterilizing and washing apparatus shown in FIG. 1 represent the preheating zone, sterilizing zone, and washing zone in respective turrets.

An embodiment of a non-inserted nozzle used in the above-described apparatus will be described below. Nozzles having nozzle mouth of the same structure can be used as the non-inserted nozzles employed in the sterilization process and non-inserted nozzles employed in the washing process, but the non-inserted nozzle employed in the sterilization process is preferably a spraying nozzle for mixing and spraying a sterilizing fluid and air. By mixing the air and sterilizing fluid and spraying the mixture, the particle size of the sprayed sterilizing fluid is reduced and the wetting characteristic of the inner peripheral surface of the container is improved. As a result, the sterilization efficiency of the sterilizing fluid is increased and the amount of the sterilizing fluid used can be decreased significantly by comparison with the conventional apparatuses. On the other hand, a nozzle for spraying only the washing fluid inside the container is preferred as a non-inserted nozzle employed in the washing process.

Figure 2:
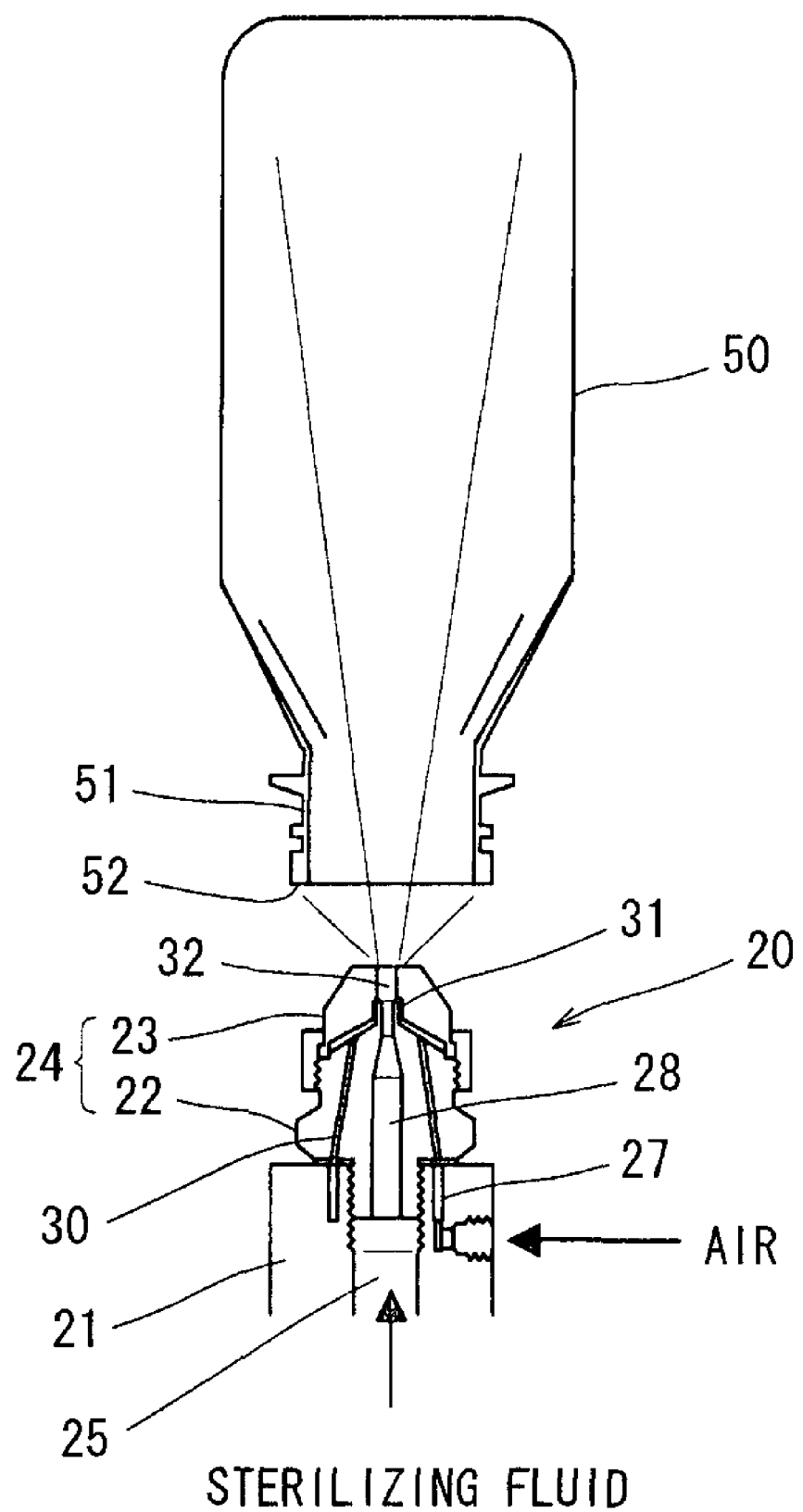
FIG. 2 is a schematic drawing illustrating a container sterilizing method using a non-inserted nozzle of an embodiment of the present invention.

FIG. 2 shows an example of a non-inserted nozzle for spraying a sterilizing fluid after the sterilizing fluid has been mixed with air and atomized; this figure illustrates schematically the state in which a bottle is sterilized with the non-inserted nozzle. A non-inserted nozzle 20 in this example is a well-known air-assist internal mixing spray nozzle in which a nozzle mouth 24 comprising a nozzle cap 22 and a cap 23 is mounted by screwing on a top section of a hollow nozzle stem 21. A sterilizing fluid channel 25 is provided in the center of the nozzle stem 21, and an air supply channel 27 that can be joined to an aseptic air supply tube, not shown in the figure, that is linked to a aseptic air source is formed in the vicinity of the top section of the sterilizing fluid channel. A sterilizing fluid spray hole 28 linked to the sterilizing fluid channel 25 and an air spray hole 30 linked to the air supply channel 27 are provided in the nozzle cap 22, and the gap between the distal end sections of the outlet ports of the holes and the cap 23 serves as a sterilizing fluid and air mixing chamber 31. The sterilizing fluid supplied to the sterilizing fluid channel 25 in a pressurized state and the air supplied to the air supply channel 27 are mixed, and the sterilizing fluid is atomized and sprayed from an orifice 32 of the cap 23.

The non-inserted nozzle 20 for sterilization is disposed, as shown in FIG. 2, below bottle holding means arranged in the sterilization turrets 4, 5, 6 shown in FIG. 1. The non-inserted nozzle 20 is disposed at a distance of 1 to 50 mm, preferably 10 to 40 mm below the lower end surface 52 of the mouth of a bottle 50 held in the bottle holding means of the sterilization turret. The arrangement position of the non-inserted nozzle is preferably such that when the sterilizing fluid is sprayed from this position, the sprayed liquid comes into contact with the inner wall of the container mouth, passes therethrough and expands inside the container, and the sterilizing fluid falls on the corner section where the bottom wall of the bottle is linked to the body section. As a result, the sprayed liquid falls on the entire surface of the bottom wall, wets the entire surface of the body section, and flows down. The distance between a lower end surface 52 of the bottle 50 and the spraying opening end of the non-inserted nozzle differs depending on the bottle mouth diameter, but the preferred distance is 10 to 40 mm. The preferred lower limit value is such that the upper end section of the nozzle does not interfere with the bottle mouth end when the bottle moves, and the upper limit value is preferably within a range where the spraying ratio inside the container is not decreased when the distance is too large, the sprayed sterilizing fluid spreads beyond the bottle mouth diameter.

FIG. 3 illustrates another embodiment of the non-inserted nozzle used in the sterilizing process. A non-inserted nozzle 35 of this embodiment pressurizes and mixes the pressurized fluid and air and atomizes and sprays the sterilizing fluid in the same manner as the non-inserted nozzle 20 of the above-described embodiment, but differs from the above-described non-inserted nozzle in that it has oblique small-diameter orifices. Common components are assigned with the same reference numerals as shown in FIG. 2 and only the differences between the two non-inserted nozzles will be explained below. A specific feature of the non-inserted nozzle 35 of the present embodiment is that a plurality of orifices 36 linked to the mixing chamber 31 are provided outwardly and obliquely in the cap 23. A plurality of the orifices 36 are formed equidistantly on a circle of radius r, which is less than the opening diameter of the container (bottle) mouth 51 that is to be sterilized at least in the vicinity of the central portion of the nozzle mouth, but if necessary one vertical orifice may be additionally provided in the central portion. The orifices 36 of the non-inserted nozzle 35 are formed obliquely at an inclination angle θ outwardly with respect to the nozzle axis. The inclination angle θ of the spray holes depends on the mouth diameter of the container, but is within a range of 2° to 10°, more preferably within a range of 3° to 7° in the case of PET bottles (mouth diameter 28 mm) with a capacity of 200 to 2000 mL. The nozzle hole 44 preferably has a small hole with a diameter of 1 to 2 mm so that the sterilizing fluid can be atomized in a jet-like fashion.

FIG. 4 shows the main portion of the non-inserted nozzle 40 in the washing process. The non-inserted nozzle 40 of the present embodiment has a nozzle mouth 42 in which the apex section of the nozzle hollow nozzle stem 41 is a liquid-receiving surface 45 of a predetermined surface area. A plurality of nozzle holes 44 passing through to a fluid channel 43 of the nozzle stem 41 are formed in the vicinity of the central portion of the nozzle mouth 42. The nozzle mouth and the nozzle stem may be entirely formed integrally from the same material, or they may be formed from separate materials and then integrated. In the present embodiment, four nozzle holes 44, as shown in FIG. 4-B, are formed equidistantly on a circle of radius r, which is less than the opening diameter of the container (bottle) mouth 51 that is to be sterilized and washed at least in the vicinity of the central portion of the nozzle mouth, but the number of the nozzles can be appropriately selected within a range of 2 to 10. It is preferred that when a washing fluid is sprayed from the downside of the container mouth, the sprayed liquid flow passes through without contacting the inner walls of the container mouth and the washing fluid comes into contact with the entire circumference of the inner surface of the bottle. For this purpose, the non-inserted nozzle 40 is disposed at a distance of 5 to 50 mm below the lower end surface 52 of the container mouth and the nozzle holes 44 are formed obliquely at an inclination angle θ outwardly with respect to the nozzle axis. The inclination angle θ of the spray holes depends on the mouth diameter of the container, but is within a range of 2°-10°, more preferably within a range of 3°-7° in the case of PET bottles (mouth diameter 28 mm) with a capacity of 200-2000 mL. The nozzle holes 44 are preferably small holes with a diameter of 1-2 mm so that the sterilizing fluid can be atomized in a jet-like fashion.

Figure 5:
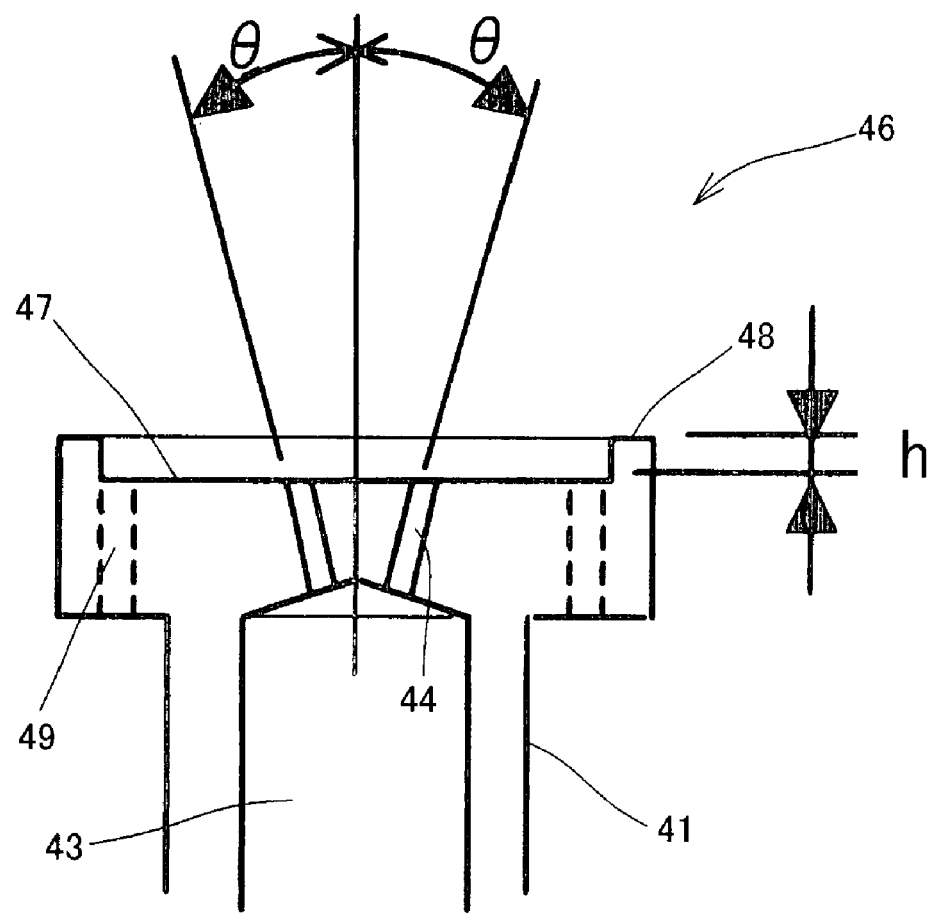
FIG. 5 is a main cross-sectional view of a non-inserted nozzle for washing of another embodiment of the present invention.

FIG. 5 shows the main portion of a non-inserted nozzle of another embodiment in the washing process. The non-inserted nozzle 46 of the present embodiment is obtained by further modifying the non-inserted nozzle shown in FIG. 4. A specific feature of this nozzle is that a retention recess is formed in the apex section of the nozzle orifice in order to increase further the juggling effect inside the container during container washing, as described hereinbelow. Components common with the non-inserted nozzle 40 of the embodiment illustrated by FIG. 4 are assigned with identical reference numerals, and only the difference between the two nozzles will be explained. The juggling effect as referred to herein is an action of the sprayed liquid that pushes up and swings the reflux liquid up and down inside the bottle that is realized when a spraying nozzle is not inserted into the bottle and a liquid is sprayed from a plurality of nozzle holes onto the inner surface of the bottle and the reflux liquid discharged from the bottle flows down along the bottle mouth and liquid-receiving surface of the nozzle or is retained thereon. The stronger is the juggling effect, the smaller is the amount of liquid required to provide for effective contact of the liquid with the entire inner surface of the bottle.

Similarly to the non-inserted nozzle of the above-described embodiment, the non-inserted nozzle 46 of the present embodiment has a liquid-receiving surface on the upper end surface of the nozzle mouth, but the liquid-receiving surface 47 of the present embodiment has a retention recess 48 with a height "h" formed on the outer periphery thereof, this retention recess being capable of retaining the fluid discharged from the container during container washing or sterilization. Furthermore, a plurality of nozzle holes 44 are formed according to the conditions identical to those of the above-described embodiment, in the retention recess. Liquid drain holes 49 are formed in the retention recess so as to be open on the outside of the outer peripheral section of the nozzle stem 41 in order to discharge rapidly the reflux liquid that was retained in the retention recess after the sterilization or washing has been completed.

An embodiment of the sterilizing and washing method in accordance with the present invention using the sterilizing apparatus of the above-described configuration will be described below.

The sterilizing fluid used in accordance with the present invention may be any one from warm water, an aqueous solution of peracetic acid, aqueous solution of hydrogen peroxide, and an aqueous solution containing hypochlorous acid, and the optimum sterilizing fluid may be selected according to the type and shape of the container and the type of the contents liquid. Furthermore, it is preferred that a container preheating step be provided prior to spraying the sterilizing fluid and that the container be heated to a surface temperature of 45 to 95° C. in order to increase the sterilization efficiency with the sterilizing fluid. However, the preheating step may be omitted. When the container surface temperature is 45° C. or less, the heating effect is small, and when the temperature is 95° C. or more, if the container is made from a synthetic resin, heat resistance thereof may decrease and the container may be thermally deformed. Accordingly, the above-described range is preferred. Preheating the sterilizing fluid may be employed instead of preheating the container. In this case, the heating temperature of the sterilizing fluid is preferably within a range of 45 to 95° C.

In the sterilizing process, a sterilizing fluid is sprayed toward the container mouth from a fixed non-inserted nozzle that is arranged below the mouth of the container clamped in an inverted posture by an inverted container clamping means disposed on a turret while the turret is being rotated. In the sterilizing fluid spraying process, the above-described non-inserted nozzle is used to mix the sterilizing fluid such as an aqueous solution of peracetic acid and air (aseptic air in the case of aseptic filling) and spraying is conducted in a two-fluid mixed state. Mixing the air with the sterilizing fluid is preferred for facilitating the atomizing of sterilizing fluid, improving wetting of the container surface and increasing the sterilization efficiency. Furthermore, as described above, spraying of the sterilizing fluid in accordance with the present invention is carried out between stages of transferring the containers between a plurality of turrets. Therefore, the feature of spraying is in not a continuous spraying but intermittent spraying by repeating spraying and termination stages. Thus, the experiments conducted by the inventors involved a case in which the sterilizing fluid was continuously sprayed with 3 sec and a case in which the 3 sec spraying time was divided into two spraying times was conduced intermittently: spraying for 1.5 sec, termination of spraying for 1 sec, and then spraying for 1.5 sec. The obtained results demonstrated that although the above two cases actually have the same spraying time and the same amount of the sterilizing fluid used, the latter case permitted the sterilizing fluid to contact with the inner wall surface of the container even within 1 sec in which the spraying was terminated and the terminating time of spraying turned out to have the equivalent sterilization effect to the time of spaying. Therefore, in the latter case, the sterilization effect obtained with a sterilizing fluid spraying time of 3 sec was identical to that obtained with a spraying time of 4 sec. Therefore, in the case of intermittent spraying, the amount of sterilizing fluid used can be greatly reduced by comparison with the continuous spraying case.

Furthermore, in the present embodiment, the sterilizing fluid was sprayed in three sterilization turrets 4, 5, 6. Therefore, when the sterilizing fluid is continuously sprayed, for example, with a spraying time in the sterilization turret 4 of 3 sec, a spraying time in the sterilization turret 5 with a smaller diameter of 2 sec, and a spraying time in the sterilization turret 6 of 3 sec, the sterilizing fluid is not sprayed within the transfer time (a total of 2 sec) between the sterilization turrets 4 and 5 and between the sterilization turrets 5 and 6, but the sterilizing fluid remains adhered to the inner wall surface of the container within this interval, which produces a sterilization effect. Therefore, in this case the sterilization time in which a sterilization effect is produced can be made 10 sec although the spraying time is 8 sec with a spraying termination time (transfer time) 2 sec. Therefore, the case of the short time spraying can allow the total time to be extended when the sterilizing fluid is attached to the container and the sterilization efficiency can be increased. Furthermore, arranging a large number of sterilization turrets makes it possible to spray the sterilizing fluid more effectively by changing the spraying conditions (spraying amount, pressure, concentration, etc.) or the shape of sterilizing nozzles (non-inserted nozzle) used in respective sterilization turrets. For example, a higher sterilization effect can be obtained by increasing the concentration of the sterilizing agent in the sterilizing fluid used in the sterilization turret 4 of the first stage and decreasing the concentration or adjusting the amount used of the sterilizing fluid that is employed in the next turret along the sterilization line.

Furthermore, the sterilization of the outer peripheral surface of the container in the sterilization process is conducted simultaneously with the sterilization of the inner surface, for example, by arranging a plurality of spraying nozzles for spraying a sterilizing fluid toward the outer peripheral surface of the container, or spraying nozzles for spraying the well-atomized mixture with the sterilizing fluid and air, in such a plurality of locations as to the outer peripheral surface of the mouth of the container, the outer peripheral surface of the container body, and the outer surface of the bottom, so that the sterilizing fluid comes into contact with the entire outer peripheral surface of the container held in an inverted posture on a turret, in the same manner as in the conventional apparatuses.

The container that has thus been subjected to sterilization is transferred to a washing turret 9 via a sterilizing fluid discharge turret 7 and a turret 8 for transferring to the washing step. In the washing process, washing of the container is performed by spraying washing water (aseptic water), but in this case it is preferred that the non-inserted nozzle is employed to have the same configuration shown in FIGS. 4 and 5 and is arranged to spray that only aseptic water without air. The non-inserted nozzle 40 for washing is fixedly arranged below the container holding means disposed for each pocket of the washing turret 9 and washing turret 11 shown in FIG. 1 and disposed at a distance of 5 to 50 mm from the lower end surface 52 of the container held by the container holding means. The non-inserted nozzle is fixed to a frame rotated integrally with the turret so that the axis center thereof matches the container axis.

While the bottle is transferred between the washing turret 9 and washing turret 11 in the washing process, a washing fluid (aseptic water in the case of aseptic filling) is sprayed from the non-inserted nozzle 40 for washing toward the bottle mouth and the inner surface is washed. In the washing process, the washing fluid sprayed from a plurality of inclined nozzle holes 44 passes through the container mouth 51, as shown in FIG. 6, falls on the corner section of the bottom part of the container, spreads over the inner surface of the bottom section and inner surface of the body wall of the container, propagates over the inner surface of the body section, becomes a reflux liquid flow 60 and flows down from the inner peripheral surface of the container mouth, whereby the washing fluid comes into contact with the entire inner surface of the container and washes off the sterilizing liquid that has adhered to the inner surface of the container. The reflux liquid flow that flowed down from the container falls on and spreads over the liquid-receiving surface 45 of the nozzle mouth 42. Therefore, part of the reflux liquid directed toward the inner side of the liquid-receiving surface interferes with the washing fluid 59 sprayed from the nozzle holes 44 and is pushed up. As a result, the sprayed flow advances into the container in a state in which the diameter of the sprayed liquid flow is larger than that in the case of simple spraying from the nozzle holes. The sprayed liquid flow that advances into the containers as a thickened flow interferes with part of the reflux liquid flowing down through the container mouth, thereby generating the juggling effect and increasing the washing effect. As a result, washing can be conducted with good efficiency and the washing water can be saved.

Furthermore, when the non-inserted nozzle 46 for washing shown in FIG. 5 is used in the washing process, because a retention recess is formed in the liquid-receiving surface 47 of the non-inserted nozzle, the interference effect of the reflux liquid retained in the retention recess and the sprayed flow of the washing water that is sprayed through the reflux liquid is further increased and a thicker sprayed liquid flow is sprayed into the container. Therefore, the juggling effect of interference with the reflux liquid in the upper zone inside the container mouth is stronger than in the case of the non-inserted nozzle 40 and the inner surface of the container can be washed with higher efficiency.

An embodiment of the present invention was explained below. However, the present invention is not limited to the above-described embodiment and various modifications can be made within a range of the technical concept thereof. For example, in the above-described embodiment rapid temperature drop of the sterilizing fluid coming into contact with the container during a sterilization process was prevented by providing a preheating step and heating the container prior to the sterilization step, but in addition to the preheating step or instead of the preheating step, the line through which the container passes in the sterilization step may be covered with a tunnel-like shielding material, the inside of the tunnel-like shielding material may be heated, for example, by installing a heater or the like, and the sterilizing fluid may be sprayed, while maintaining the heated atmosphere.

EXAMPLE

A test sample bottle with bacteria adhered thereto was fabricated, the sample bottle was sterilized and washed under the below-described conditions by assuming the sterilization apparatus with a turret configuration shown in FIG. 1 and the sterilization effect was checked by studying the number of living bacteria by incubation.

Bottle: 500 mL PET bottle.

Sterilizing agent: Sterilizing agent Toyo-aktiv of a peracetic acid system.

Concentration of peracetic acid: 2000 ppm.

Temperature: the sterilizing agent is sprayed so that the temperature of the inner surface of the bottle reaches 65° C.

Non-inserted nozzle: air-assisted internal mixing sprayer.

Flow rate of sterilizing agent: sprayed liquid quantity 0.27 L/min (0.15 MPa).

Air flow rate and temperature: sprayed air quantity 15 NL/min (0.07 MPa), 30° C.

Distance between the bottle mouth and non-inserted nozzle: 30 mm.

Sterilization time: see the First Example in Table 1 (3 sec of spraying-1 sec of termination-2 sec of spraying-1 sec of termination-3 sec of spraying).

Bottle washing after sterilization: implemented with aseptic water at a temperature of 30° C.

The bottle was washed by spraying aseptic water onto the inner surface of the inverted bottle at 67 mL/sec×3 sec so that no sterilizing agent remained on the inner surface of the bottle after sterilization. The non-inserted nozzle shown in FIG. 3 was disposed 15 mm below the bottle mouth, and the aseptic water sprayed from the nozzle was arranged to fall on the entire inner surface of the bottle and to be discharged from the bottle mouth.

Fabrication of Bottle with Test Bacteria:

Test bacteria: *Geobacillus stearothermophilus* ATCC7953

A suspension of the sample bacteria was prepared to the predetermined concentration, sprayed by a sprayer with 0.3 mL/unit onto the inner surface of a bottle so as to obtain the initial number of bacteria of $3.7 \times 10^6$ cfu/bottle, and caused to adhere to the inner surface of the bottle. The bottle was held for 24 h in a clean room (CLASS 1000), and the inner surface of the bottle was dried. The fabricated bottle was passed successively through a sterilizing apparatus and washing apparatus and sealed with a sterilized cap.

Method for counting living bacteria: 500 mL of SCD liquid culture was charged.

After holding for 7 days at 30° C., the specimens where the culture was clouded were considered positive (+) and those where no opacity was observed in the culture were considered negative (−).

The test was conducted on five specimens. The results are shown in Table 2.

COMPARATIVE EXAMPLE

As a comparative example, the sterilization effect was studied in the same manner as described above with respect to the case where sterilization was conducted by changing only the spraying conditions of the sterilizing fluid with respect to those of the above-described example, as shown in Table 1, other conditions being the same. In the comparative example, spraying of the sterilizing fluid for sterilizing the inner surface of the bottle was conducted continuously for 10 sec (Comparative Example 1) or continuously for 8 sec (Comparative Example 2), rather than intermittently, and the sterilization effect was studied. The results are shown together with those of the above-described example in Table 2.

Test Results

As follows from Table 2, in the Example, all the sample bottles were negative and good sterilization was confirmed. A total spraying time of sterilization agent in the Example was 8 sec and the total sterilization time was 10 sec.

By contrast, in Comparative Example 1, that is, when spraying of the sterilizing fluid was conducted continuously for 10 sec, the sterilization effect identical to that of Example was obtained, but in Comparative Example 2, that is, when spraying was continuously conducted for 8 sec, living bacteria were found on some containers, as shown in Table 2, and sterilization by spraying for 8 sec was found to be incomplete.

As described above, the spraying time (that is, sprayed amount) of the sterilizing fluid in the Example and Comparative Example 2 was the same, but in Example, absolutely no living bacteria were observed, and a sterilization effect was found to be identical to that obtained by spraying for 10 sec in Comparative Example 1, despite the fact that the spraying time in Example was 8 sec. The above-described results demonstrated that the sterilization method in accordance with the present invention demonstrated a significant effect in terms of saving the sterilizing fluid.

TABLE 1

| TEST CONDITIONS | TIME (sec) | | | | | TOTAL TIME (sec) | |
| --- | --- | --- | --- | --- | --- | --- | --- |
| | SPRAYING 1 | TERMINATION 1 | SPRAYING 2 | TERMINATION 2 | SPRAYING 3 | TOTAL SPRAYING | TOTAL TERMINATION |
| EXAMPLE | 3 | 1 | 2 | 1 | 3 | 8 | 2 |
| COMPARATIVE EXAMPLE 1 | 10 | 0 | 0 | 0 | 0 | 10 | 0 |
| COMPARATIVE EXAMPLE 2 | 8 | 0 | 0 | 0 | 0 | 8 | 0 |

TABLE 2

| TEST RESULTS | PRESENCE OR ABSENCE OF LIVING BACTERIA | | | | |
| --- | --- | --- | --- | --- | --- |
| | 1 | 2 | 3 | 4 | 5 |
| EXAMPLE | (−) | (−) | (−) | (−) | (−) |
| COMPARATIVE EXAMPLE 1 | (−) | (−) | (−) | (−) | (−) |
| COMPARATIVE EXAMPLE 2 | (+) | (−) | (−) | (−) | (−) |

Industrial Applicability

The container sterilizing and washing method and apparatus in accordance with the present invention are especially advantageous for sterilization in an aseptic filling system for bottles, but the application thereof is not limited to aseptic filling and they can be used in sterilization apparatuses and washing apparatuses for containers when the containers are sterilized, washed, and filled, such as hot pack or usual normal-temperature filling. Furthermore, the method and apparatus are applicable to containers of any shape including round or angular bottles and also can be used for sterilizing and washing containers of various materials such as plastics, metals, and glass.

The invention claimed is:

1. A method for sterilizing and washing a container, comprising:
    sterilizing the inside of a container that is conveyed in an inverted posture, and
    washing the inside of the container that is conveyed in an inverted posture,
    wherein in said sterilizing, a non-inserted nozzle is disposed below a mouth of the container conveyed in an inverted posture at a distance of 1-50 mm therefrom,
    wherein in said sterilizing, a sterilizing fluid is atomized and sprayed from said non-inserted nozzle into the container onto an inner surface of the container, thereby wetting the inner surface of the container,
    wherein the sterilizing of the container is divided such that it is carried out at a plurality of sterilization turrets,
    wherein in said sterilizing carried out at the plurality of sterilization turrets, sterilizing fluid is continuously sprayed onto the inner surface of the container in a respective sterilization turret for a predetermined time, spraying of the sterilizing fluid is stopped at least in an interval in which the container is transferred from the respective sterilization turret to the next sterilization turret, thereby sterilizing the inner surface of the container by intermittent spraying performed by alternately spraying the sterilizing fluid and terminating the spraying, and
    wherein in said washing, a non-inserted nozzle is disposed below the mouth of the container conveyed in an inverted posture at a distance of 5-50 mm therefrom, washing water is sprayed from said non-inserted nozzle into the container, thereby washing the inner surface of the container.

2. The method for sterilizing and washing a container according to claim 1, wherein said sterilizing fluid is selected from the group consisting of warm water, an aqueous solution of peracetic acid, aqueous solution of hydrogen peroxide, and an aqueous solution containing hypochlorous acid.

3. The method for sterilizing and washing a container according to claim 1, further comprising:
    preheating the container prior to said sterilizing.

4. The method for sterilizing and washing a container according to claim 1, wherein in said sterilizing, a heated sterilizing fluid is sprayed onto the outer surface of the container from one or a plurality of sterilizing nozzles toward the outer surface of the container, thereby wetting the outer surface of the container with an atomized sterilizing fluid.

5. The method for sterilizing and washing a container according to claim 1, wherein a container surface temperature in said sterilizing is adjusted to 45-90° C.

6. The method for sterilizing and washing a container according to claim 1, wherein said plurality of sterilization turrets have mutually different diameters and different sterilization times.

7. The method for sterilizing and washing a container according to claim 1,
    wherein each of said plurality of sterilization turrets include a sterilizing zone and a nonsterilizing zone, and wherein said transferring of said container from one of said plurality of sterilization turrets to the next one of said plurality of sterilization turrets is performed at a position corresponding to the non-sterilizing zones of each sterilization turret.

8. The method for sterilizing and washing a container according to claim 1, wherein the sterilizing fluid sprayed by the non-inserted nozzle in one of said plurality of sterilization turrets is of a different concentration, amount or pressure as compared to the sterilizing fluid sprayed by the non-inserted nozzle in the other sterilization turrets.

9. The method for sterilizing and washing a container according to claim 1, wherein the non-inserted nozzle in one of said plurality of sterilization turrets is of a different shape as compared to the non-inserted nozzle in the other sterilization turrets.

* * * * *